(12) United States Patent
Ko et al.

(10) Patent No.: US 12,148,604 B2
(45) Date of Patent: Nov. 19, 2024

(54) METHOD FOR GENERATING DATA SET FOR TRAINING A PREDICTION MODEL AND APPARATUS COMPRISING THE PREDICITON MODEL

(71) Applicant: AMIT, Inc., Seongnam-si (KR)

(72) Inventors: Chung-Kon Ko, Seongnam-si (KR); Chang-No Kwon, Yongin-si (KR); Kyung-Jin Kim, Yongin-si (KR)

(73) Assignee: AMIT, Inc., Seongnam-si (KR)

( * ) Notice: Subject to any disclaimer, the term of this patent is extended or adjusted under 35 U.S.C. 154(b) by 1187 days.

(21) Appl. No.: 16/855,155

(22) Filed: Apr. 22, 2020

(65) Prior Publication Data

US 2020/0335315 A1   Oct. 22, 2020

(51) Int. Cl.
| | |
|---|---|
| *H01J 49/00* | (2006.01) |
| *G06F 18/21* | (2023.01) |
| *G06F 18/214* | (2023.01) |
| *G06N 3/08* | (2023.01) |
| *G06N 5/02* | (2023.01) |
| *G06N 5/04* | (2023.01) |
| *G06V 10/82* | (2022.01) |
| *G16H 10/40* | (2018.01) |
| *G16H 50/20* | (2018.01) |
| *G16H 70/60* | (2018.01) |

(52) U.S. Cl.
CPC ........ *H01J 49/0036* (2013.01); *G06F 18/214* (2023.01); *G06F 18/217* (2023.01); *G06N 3/08* (2013.01); *G06N 5/02* (2013.01); *G06N 5/04* (2013.01); *G06V 10/82* (2022.01); *G16H 10/40* (2018.01); *G16H 50/20* (2018.01); *G16H 70/60* (2018.01)

(58) Field of Classification Search
CPC .. H01J 49/0036; G06F 18/214; G06F 18/217; G06F 18/24133; G06F 2218/10; G06N 3/08; G06N 5/02; G06N 5/04; G06N 3/044; G06N 3/045; G06V 10/82; G16H 10/40; G16H 50/20; G16H 70/60; G16H 50/30

See application file for complete search history.

(56) References Cited

U.S. PATENT DOCUMENTS

| | | | |
|---|---|---|---|
| 9,343,276 B2 * | 5/2016 | Tate | G01N 30/72 |
| 2005/0054005 A1 * | 3/2005 | Ellis | G01N 33/564 |
| | | | 435/7.1 |
| 2008/0153928 A1 * | 6/2008 | van Ravenzwaay | A01K 29/00 |
| | | | 514/789 |
| 2008/0237457 A1 * | 10/2008 | Yamashita | H01J 49/0036 |
| | | | 250/281 |

(Continued)

FOREIGN PATENT DOCUMENTS

| | | | | |
|---|---|---|---|---|
| CN | 105738526 A | * | 7/2016 | |
| WO | WO-2005106038 A2 | * | 11/2005 | ............. C07K 16/18 |
| WO | WO-2007014825 A1 | * | 2/2007 | ............. A01K 1/031 |

*Primary Examiner* — Joseph J Dallo
(74) *Attorney, Agent, or Firm* — AJU IP Global PLLC

(57) ABSTRACT

The present invention relates to a method for generating a data set for predictive model training and an apparatus including the predictive model. A data set generating method according to the present invention comprises the steps of: extracting valid data from mass-strength data for an input sample, detecting peak points from the valid data, and obtaining peak data for the detected peak points. And generating an input array based on the peak data.

15 Claims, 9 Drawing Sheets

(56) References Cited

U.S. PATENT DOCUMENTS

Figure 1:
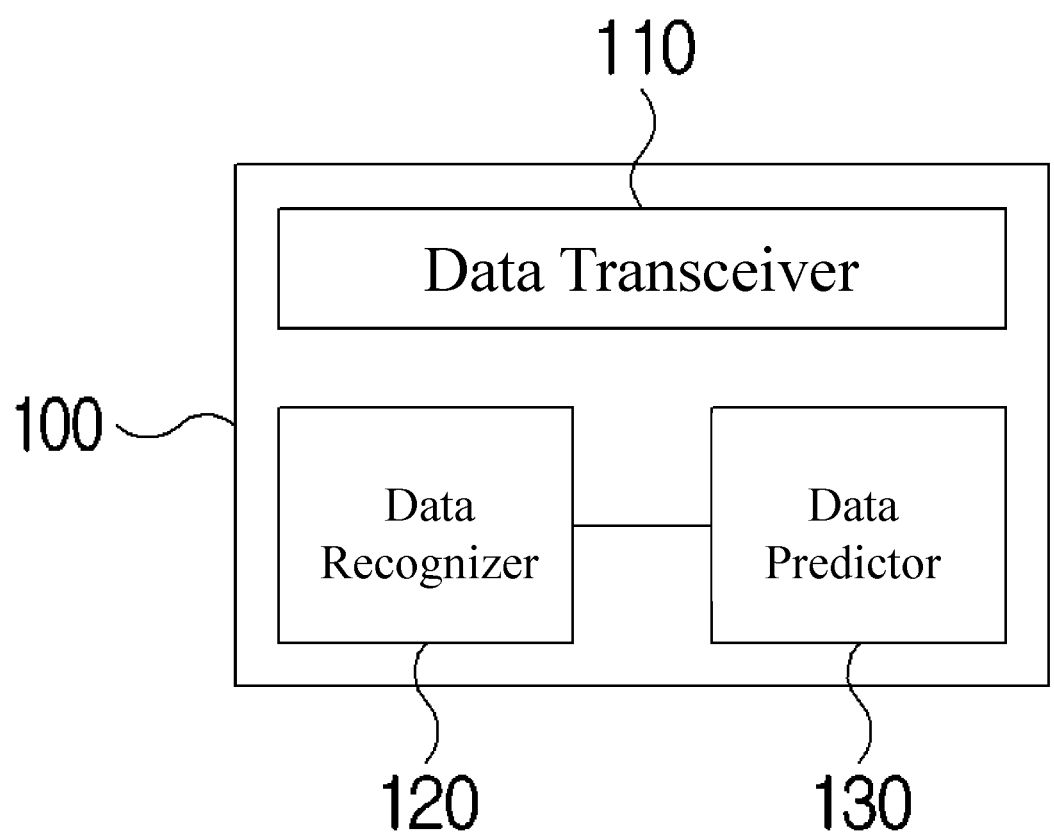

2016/0025691 A1* 1/2016 Taneda .................. G01N 30/72
702/23
2017/0047209 A1* 2/2017 Bailey .................... G01N 30/72
2017/0358434 A1* 12/2017 Matsuura ............... G16C 20/70

* cited by examiner

METHOD FOR GENERATING DATA SET FOR TRAINING A PREDICTION MODEL AND APPARATUS COMPRISING THE PREDICITON MODEL

The present application claims priority to Korean Patent Application No. 10-2019-0046836 filed on Apr. 22, 2019, which is hereby incorporated by reference in its entirety.

BACKGROUND

Embodiments relate to a method for generating a data set for predictive model training and/or an apparatus including the predictive model.

Artificial intelligence forecasting systems may simplify medical diagnostic procedures and catch early onset factors. Such a prediction system may be implemented through artificial intelligence, which collects data using cloud computing and/or learned based on the collected data.

In order to increase the reliability of prediction results through artificial intelligence, it is important to collect various learning data and process it into a form of data suitable for deep neural network training. However, due to the complexity of the data in the medical field, it may be challenging to convert medical field data into data sets for deep neural network training.

SUMMARY

An object of embodiments is to provide a data set generation method for increasing the reliability of medical factor prediction and a prediction apparatus trained by the data set. An object of embodiments is to provide a method of processing information utilized in a prediction task to generate a data set for further training.

Technical challenges addressed by embodiments are not limited to the above-mentioned technical challenges, and other technical challenges not mentioned above will be clearly understood by those skilled in the art from the following description.

A data set generation method according to embodiments may include extracting valid data from mass-strength data for an input sample, detecting a peak point from the valid data, acquiring peak data from the detected peak point, and/or generating an input array based on the peak data. In embodiments, the valid data may include mass-strength data in which a mass value is in a preset range.

In embodiments, a method may include generating a data set. A peak point may be determined by comparing an effective intensity value of a first point with an effective intensity value of neighboring points adjacent to the first point, and thus determining the first point. In embodiments, a method may include determining whether or not a peak point exists.

In embodiments, a method for generating a data set may include obtaining the effective intensity value by subtracting a reference value of a first point from the intensity value of a first point.

In embodiments, when an intensity value of a first point is larger than a reference value of a zero point, which is a previous point of the first point, the same intensity value as the first point and the first point is obtained. Based on the width between the second points having, it may be determined whether the reference value of the zero point is set equal to the reference value of the first point.

In the method for generating a data set according to embodiments, the peak data includes a relative intensity value of the peak point or a scaled relative intensity value, and the relative intensity value of the first peak point is the maximum value among the effective intensity values of the peak points and the effective strength value at the first peak point.

In the method for generating a data set according to embodiments, the N-th data of the input array may represent the relative intensity value or the scaled relative intensity value in the N-th section of the preset range.

In embodiments, a method for generating a data may be performed when there are a plurality of peak points in the N-th section, the average value, the maximum value, the minimum value of the relative intensity values, or the scaled relative intensity values of the plurality of peak points are the N-th data.

The prediction device according to embodiments may include a data recognizing unit for converting peak data of a mass spectrometric result of an input sample into an input array for deep neural network input, and inputting the input array to the deep neural network, and responding to the input. The apparatus may include a data predictor configured to output a prediction result for the input sample and generate inference data based on the prediction result.

In the prediction apparatus according to the present invention, the inference data may be generated based on a first prediction result for the input array and a second prediction result for the input array.

In the prediction apparatus according to embodiments, when the first prediction result is a lower element of the second prediction result, the inference is determined to include at least one of the first prediction result or the second prediction result. If the first prediction result is not a sub-element of the second prediction result, the inference data may be configured to include information indicating a prediction failure.

In the prediction apparatus according to embodiments, the first prediction result may indicate a species of the input sample, and the second prediction result may indicate a genus of the input sample.

In the prediction apparatus according to embodiments, the data predictor further trains the deep neural network based on learning data accumulated in a predetermined period or a predetermined number of learning data, and the learning data is the input array and the input data. Including correct answer information for the sample, the correct answer information may be referred to the clinical data registered in the clinical pathology system.

In the prediction apparatus according to embodiments, the peak data includes a relative intensity value of the peak point or a scaled relative intensity value, and the relative intensity value of the first peak point is the maximum value of the effective intensity values of the peak points and the first value. In embodiments, peak data may be determined based on the ratio between the effective intensity values at one peak point.

In the prediction apparatus according to embodiments, the N-th data of the input array may represent the relative intensity value or the scaled relative intensity value in the N-th section of a preset range.

In the prediction apparatus according to the present invention, when a plurality of peak points exist in the N-th section, an average value, a maximum value, or a minimum value of the relative intensity values or the scaled relative intensity values of the plurality of peak points are set as the N-th data.

The features briefly summarized above with respect to embodiments are merely illustrative aspects of the detailed description that follows, and do not limit the scope of embodiments of the invention.

Embodiments relate to a method of converting medical data into a data set for deep neural network learning, thereby improving reliability of a prediction device for predicting an onset factor.

According to embodiments, the reliability of the prediction apparatus can be improved by converting the information utilized in the prediction task into a data set for further training.

Effects obtained in the embodiments are not limited to the above-mentioned effects, and other effects not mentioned above may be clearly understood by those skilled in the art from the following description.

DRAWINGS

Example FIG. 1 is a block diagram of an inspection apparatus, in accordance with embodiments.

Figure 2:
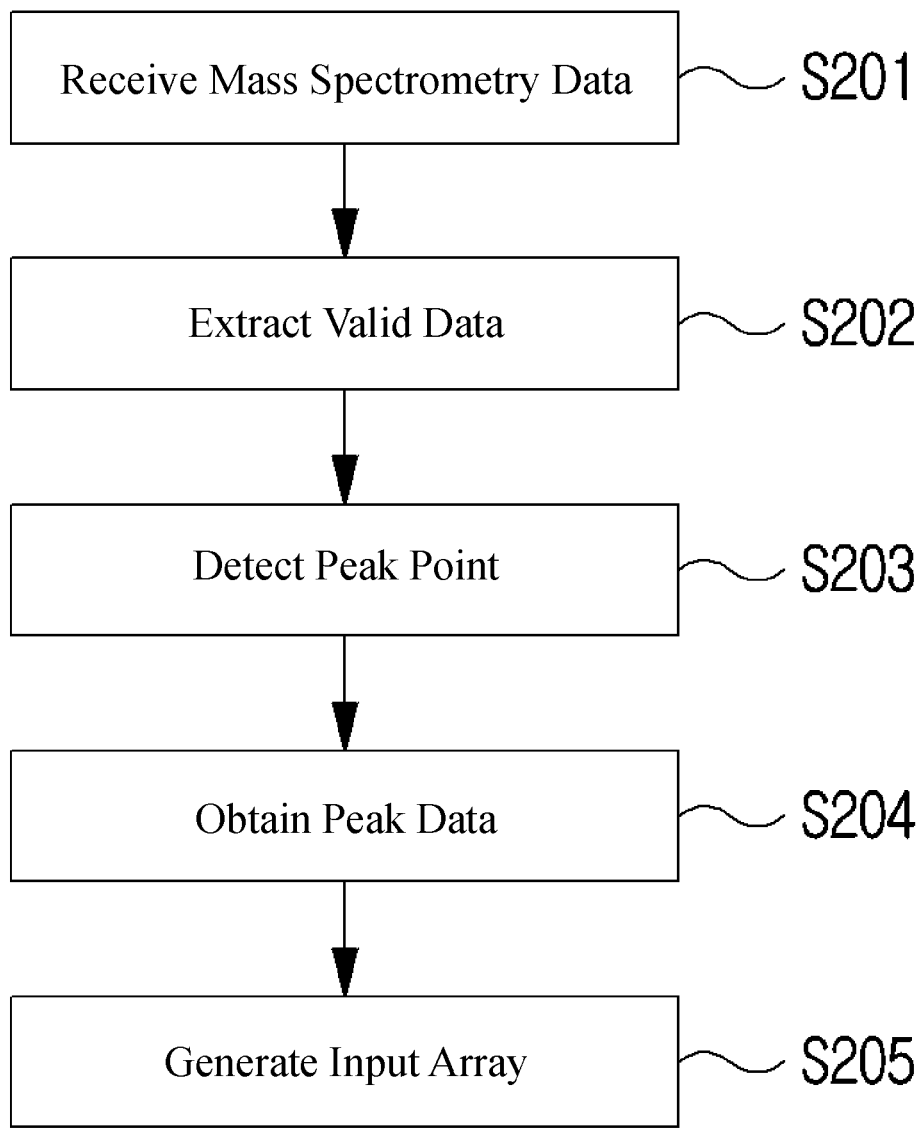

Example FIG. 2 is a flowchart illustrating a data set generation method for deep neural network training, in accordance with embodiments.

Figure 3:
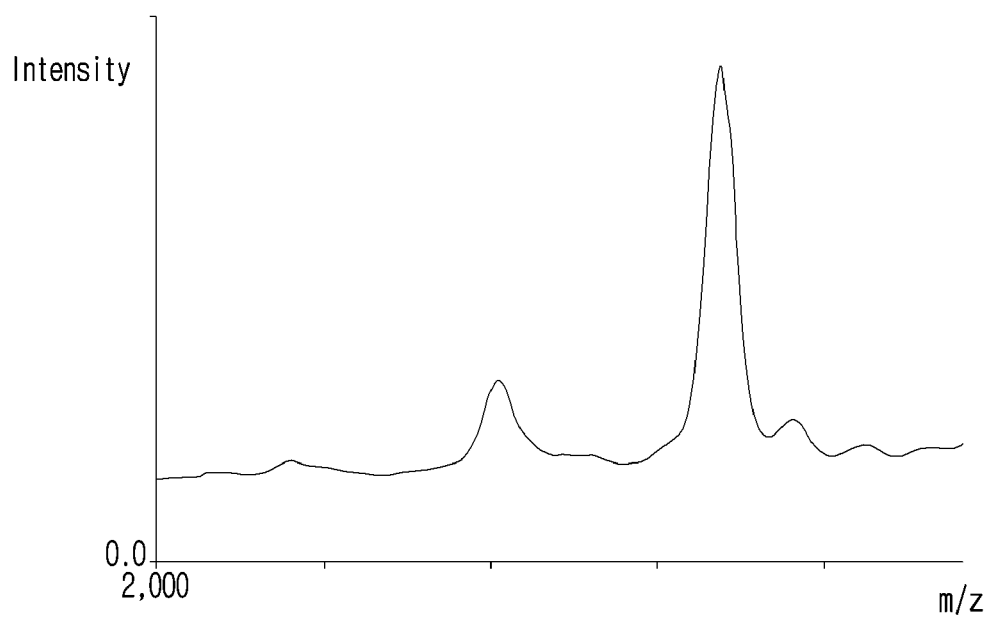

Example FIG. 3 illustrates a graph according to mass-strength data, in accordance with embodiments.

Figure 4:
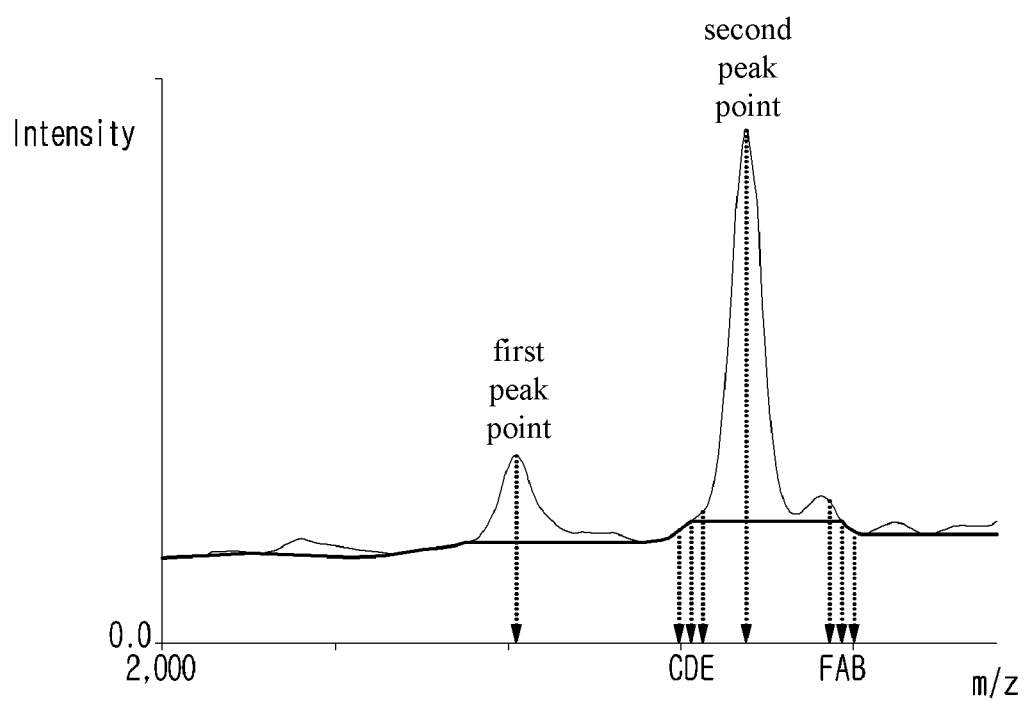

Example FIG. 4 is a diagram for explaining an example of determining a reference value, in accordance with embodiments.

Figure 5:
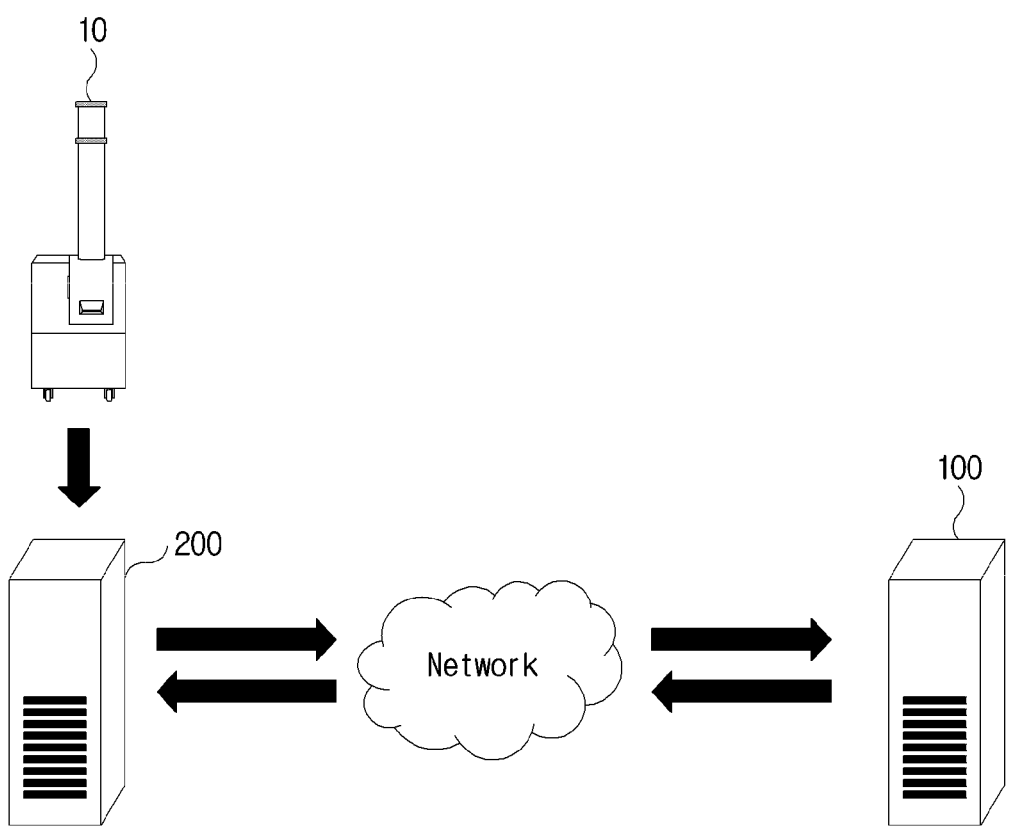

Example FIG. 5 is a diagram illustrating an artificial intelligence-based prediction system, in accordance with embodiments.

Figure 6:
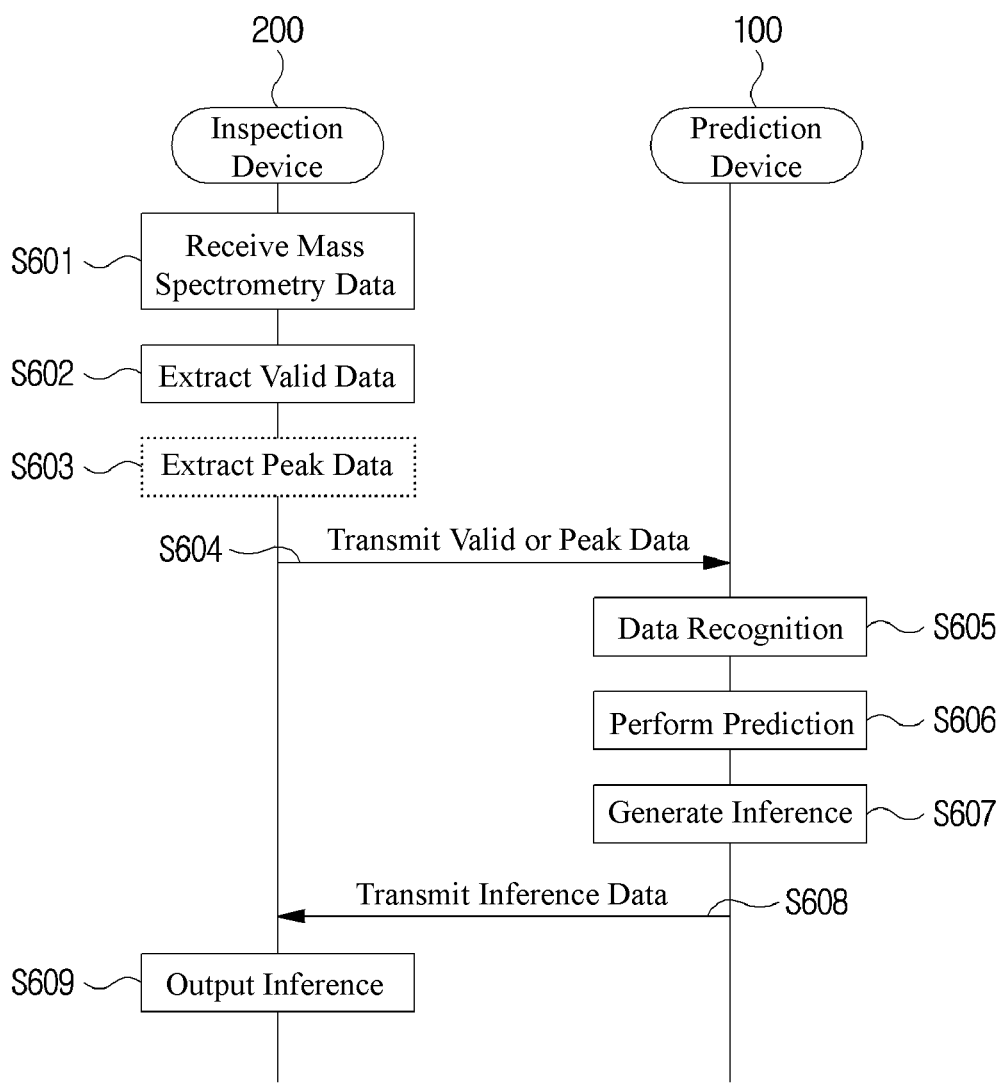

Example FIG. 6 shows a workflow between the devices shown in FIG. 5, in accordance with embodiments.

Figure 7:
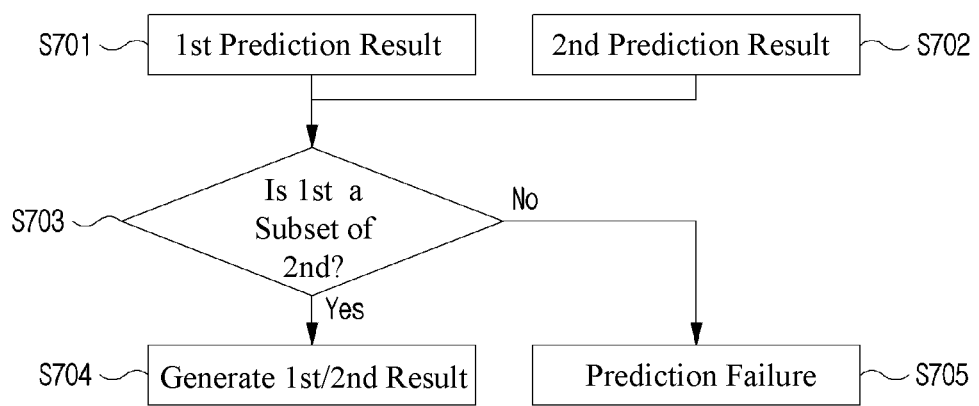

Example FIG. 7 is a flowchart illustrating a process of generating inference data, in accordance with embodiments.

Figure 8:
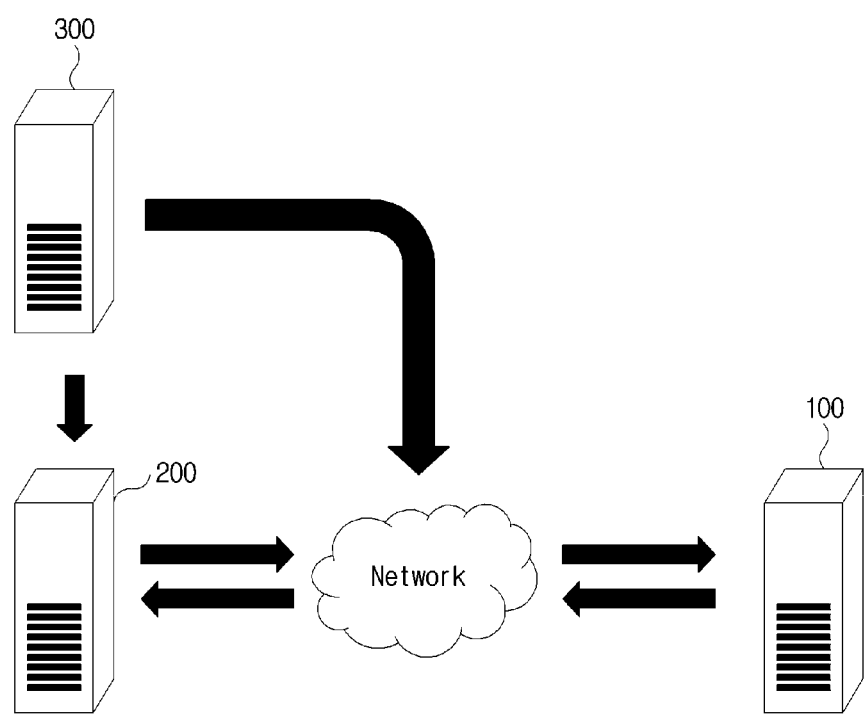

Example FIG. 8 is a diagram illustrating a learning data management system, in accordance with embodiments.

Figure 9:
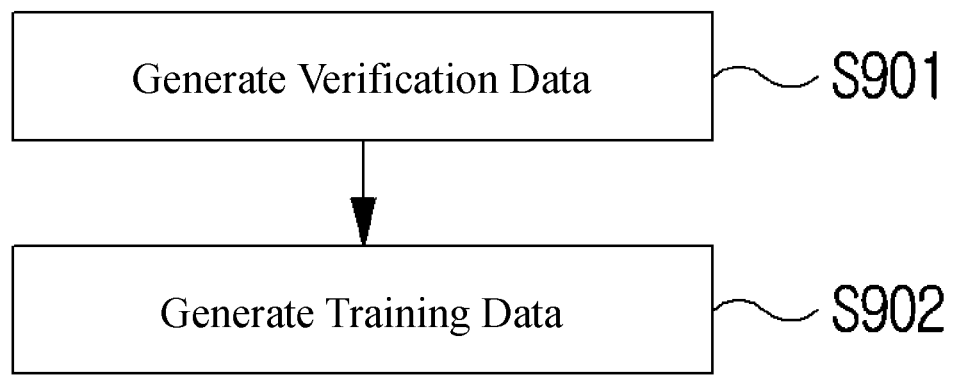

Example FIG. 9 is a flowchart illustrating a process of generating learning data in the verification apparatus, in accordance with embodiments.

DESCRIPTION

As the invention allows for various changes and numerous embodiments, particular embodiments will be illustrated in the drawings and described in detail in the written description. However, this is not intended to limit the present invention to specific embodiments, it should be understood to include all modifications, equivalents, and substitutes included in the spirit and scope of the present invention. In describing the drawings, similar reference numerals may used for similar elements in a non-limiting fashion.

The terminology used herein is for the purpose of describing particular example embodiments only and is not intended to be limiting of the present invention or the claims. Singular expressions include plural expressions unless the context clearly indicates otherwise. In this application, the terms comprise or have are intended to indicate that there is a feature, number, step, operation, component, part, or combination thereof described in the specification, and one or more other features. It is to be understood that the present invention does not exclude the possibility of the presence or the addition of numbers, steps, operations, components, components, or a combination thereof.

Hereinafter, in the embodiments described, the device may be a computing device capable of storing, computing, and processing data. The computing device may be a stationary device such as a PC, server or workstation, or a mobile device such as a laptop, tablet, smartphone or PDA.

The apparatus may include a memory for storing data, an input/output unit for data input/output, a communication unit for data transmission and reception, and a control unit for data operation. The memory stores data for driving the device and executing specific commands. The configuration of each device to be described later may be implemented by the above-listed components or a combination thereof. In addition, the above-listed components may be implemented by hardware, software, or a combination thereof.

In embodiments, the interval between the first point and the second point is a section in which mass/time is greater than or equal to the first point and less than the second point, a section in which mass/time is greater than or equal to the first point and less than or equal to the second point, or a section in which the mass/time exceeds the first point and less than the second point.

Hereinafter, example flowcharts may represent a data processing process in the apparatus. In example flowcharts, a data processing process may be described in a specific order, but embodiments include data processing that is performed in a different order from that described in the example flowcharts.

Embodiments relate to an inspection device including a predictive model trained using a learning algorithm and a prediction system for predicting an input sample using the inspection device. Hereinafter, an example inspection apparatus and the prediction system will be described in accordance with embodiments.

Example FIG. 1 is a block diagram of a prediction apparatus, in accordance with embodiments. The prediction apparatus 100 may include a data transceiver 110, a data recognizer 120, and a data predictor 130.

The data transceiver 110 may receive data from an external device and/or transmit data to the external device. The data transceiver 110 may transmit/receive data with an external device through an IP network, in accordance with embodiments.

The data recognizing unit 120 may perform data pre-processing for inputting the inspection data received from the inspection apparatus into the deep neural network. Through the preprocessing, the inspection data may be converted into a data array for a plurality of input nodes. The number of input nodes may be variably determined according to the prediction model, in accordance with embodiments.

The data predictor 130 may include a deep neural network based prediction model. The deep neural network may be configured based on at least one of a recurrent neural network (RNN), a convolutional neural network (CNN), or a basic neural network. When inspection data is input to the input node, the input inspection data may be predicted, and a prediction result value may be output. The prediction may be performed based on a deep neural network based prediction model. The predictive model may be used to output microbial prediction, disease prediction of a clinical investigator, or antibiotic susceptibility prediction of a clinical investigator corresponding to an input sample.

The predictive model may be trained based on a data set generated based on mass spectrometry data. Referring to the drawings, a data set generation method for training a deep neural network based prediction model will be described in detail.

Example FIG. 2 is a flowchart illustrating a data set generation method for deep neural network training, in accordance with embodiments. FIG. 2 may be processed in an apparatus capable of processing data. The apparatus may be the prediction apparatus 100 illustrated in FIG. 1 or a computing device capable of communicating with the prediction apparatus 100.

The data set for predictive model training may include an input array and/or an output array. The input array may be generated based on the mass spectrometry data of the mass spectrometer.

The mass spectrometer performs mass spectrometry on the input sample. For example, the mass spectrometer may perform mass spectrometry on an input sample in a matrix-assisted laser desorption/ionization time-of-flight (MALDI-TOF) method. The MALDI-TOF irradiates the sample with a laser and outputs at least one of the sample's time-intensity data or the sample's mass-strength data based on the flight time of the ionized material. The time-strength data records the intensity values for each time point, and the mass-strength data records the intensity values for each mass point. Here, the mass may be expressed in units of mass to charge (m/z).

The computing device receives mass spectrometry data from the mass spectrometer (S201). The mass spectrometry data may include at least one of time-strength data or mass-strength data of the input sample. The computing device may obtain mass-strength data based on the time-strength data and/or obtain time-strength data based on the mass-strength data.

Example FIG. 3 illustrates a graph according to mass-strength data, in accordance with embodiments.

The computing device may extract valid data from the mass spectrometry data received from the mass spectrometer (S202). As an example, the computing device may extract mass-strength data within the preset range of the mass value as valid data. Alternatively, the inspection apparatus may extract time-intensity data within a predetermined range of time values as valid data.

For example, the preset range may be a section between 2,000 m/z and 20,000 m/z or a section between 3,000 m/z and 30,000 m/z. In embodiments, the preset range may be determined according to the type of prediction model to be trained. As an example, the preset range for the prediction model for microbial prediction may be set to a section between 2,000 m/z and 20,000 m/z. On the other hand, the preset range for the prediction model for disease prediction may be set to a section between 3,000 m/z to 20,000 m/z, as an alternative example.

The computing device may detect a peak point of the intensity in the valid data (S203) and obtain the peak data (S204). The peak data may include location information of peak points and intensity information at each peak point. The position information indicates at least one of time or mass at the peak point, and the intensity information indicates at least one of an effective intensity value, a relative intensity value or a scaled relative intensity value at the peak point.

The computing device may detect the peak point based on the effective intensity value at each point. Here, points represent arbitrary mass/time points. The effective intensity value may be derived by subtracting the reference value from the intensity value at the peak point. For example, when the effective intensity value of the first point is greater than the effective intensity value of neighboring points, the first point may be determined as the peak point. Here, the neighboring points may include a previous point and a subsequent point of the first point.

However, even when the effective intensity value of the first point is greater than the effective intensity value of the neighboring points, it may be determined that the first point is not the peak point if the effective intensity value of the first point is smaller than the threshold value. This is to prevent the noise from being recognized as the peak point.

The reference value for calculating the effective intensity value is a variable that is determined based on the intensity value of each point.

Example FIG. 4 is a diagram for explaining an example of determining a reference value, in accordance with embodiments.

First, the reference value at any point may be set below the intensity value at any point. For example, when the reference value of the first point is greater than the intensity value of the second point, the reference value of the second point may be updated with the intensity value of the second point without inheriting the reference value of the first point. Here, the first point and the second point represent two consecutive points in the valid data. Referring to the example illustrated in FIG. 4, since the intensity value of the point B is smaller than the reference value of the point A, the reference value of the point B may be updated with the intensity value of the point B.

If the intensity value of any point is greater than the reference value of the previous point, it may be determined whether to update the reference value based on the width between any point and the next point having the same intensity value. Here, the width represents the mass/time difference between any point and the next point. For example, when a width between an arbitrary point and a next point is larger than a threshold value, the reference value of the arbitrary point may be updated with an intensity value. On the other hand, when the width between the arbitrary point and the next point is smaller than the threshold value, the reference value of the arbitrary point may be set to be the same as the reference value of the previous point. In the example shown in FIG. 4, the intensity value at point D is greater than the reference value at point C. In this case, it is possible to determine whether to update the reference value at the D point by comparing the width between the D point and the A point having the same intensity value as the D point with the threshold value. When the width between the D point and the A point is larger than the threshold value, the reference value of the D point may be set equal to the intensity value of the D point.

At point E having an intensity value greater than the reference value of point D, it is possible to determine whether to update the reference value by comparing the width between point E and point F with a threshold value. When the width between the point E and the F point is smaller than the threshold value, the reference value of the point E may be set equal to the point D.

When a peak point is detected, the effective intensity value of each peak point can be converted into a relative intensity value. Specifically, the maximum value of the effective intensity values of the peak points may be determined, and the relative intensity value at each peak point may be calculated based on the ratio between the maximum value and the effective intensity value of each peak point. In the example shown in FIG. 4, when an effective intensity value 400 at the second peak point is determined as the maximum value, the effective intensity value 100 at the first peak point is converted into a relative intensity value of 0.25 (100/400), and the effective intensity value 400 at the two peak points can be converted to the relative intensity value 1.

In order to convert the relative intensity values to integer data, the relative intensity values may be scaled. As an example, scaling may be performed by multiplying the relative intensity value by 10 N. Here, N may be one or more natural numbers.

Based on the peak data, an input array for deep neural network training may be generated (S205). In detail, the computing device may generate the input array by recording the intensity information in units of predefined intervals. The interval unit may be determined according to the number of input nodes of the deep neural network. For example, when the interval unit is 10 m/z, an input array including about 1,800 pieces of data in a range of 2,000 m/z to 20,000 m/z may be generated. Here, the intensity information may be at least one of an effective intensity value, a relative intensity value, or a scaled relative intensity value. For example, when the interval unit is 10 m/z, the Nth data in the data array is a scaled relative intensity value between (2,000+10 (N−1)) m/z to (2,000+10N) m/z intervals can be represented. If no peak is detected in the N-th section of the preset range, the N-th data may be set to a default value. Preferably, the default value may be zero. If a plurality of peak points exist in the N-th section, a maximum, minimum or average value of the intensity values of the plurality of peak points may be allocated to the N-th section. For example, when 3,001 m/z and 3,008 m/z in the interval between 3,000 m/z and 3,010 m/z are determined as the peak points, the intensity values of the 3,001 m/z peak points and the 3,008 m/z peak points are the maximum values. The maximum value, the minimum value, or the average value of the intensity values may be allocated as data in the interval between 3,000 m/z and 3,010 m/z.

The actual data of the sample on which the mass spectrometry has been performed should be trained with the correct answer for the input array generated. Accordingly, the output array can be configured such that actual data of the sample is allocated to the output node. Here, the actual data may be the type of bacteria, whether or not the disease is retained corresponding to the clinical sample, the disease progression corresponding to the clinical sample, or the antibiotic sensitivity corresponding to the sample. The type of bacterium may refer to a genus or bacterial species of the bacterium. The disease may indicate the type of cancer, such as liver cancer, stomach cancer, lung cancer. Disease progression may indicate normal, borderline cancer, stage 1, 2, 3 or 4, and the like.

Based on the mass spectrometry results for N materials, N or more input arrays may be configured, and based on actual data of each of the N materials, an output array including N data may be configured. The resulting input array set and output array can be configured into one data set to train the predictive model.

Multiple mass spectrometry may be performed on one substance and a plurality of input data arrays may be generated from the plurality of mass spectrometric data. That is, a plurality of input arrays can generate a data set pointing to the same correct answer.

The data set can be used to train the predictive model, and the trained predictive model can be used to perform predictions on the samples entered into the mass spectrometer. Hereinafter, a prediction system for performing prediction on an input sample using a trained prediction model will be described in detail.

Example FIG. 5 is a diagram illustrating an artificial intelligence-based prediction system according to embodiments. Example FIG. 6 illustrates a workflow between the devices illustrated in FIG. 5. Based on FIG. 6, operation of each device shown in FIG. 5 will be described in detail.

Referring to FIG. 5, the prediction system according to embodiments may include a mass analyzer 10, an inspection device 200, and a prediction device 100.

The mass spectrometer 10 performs mass spectrometry on the input sample and outputs mass spectrometry data as a result of the mass spectrometry. The mass spectrometry data may include at least one of time-strength data or mass-strength data of the input sample.

The inspection apparatus 200 receives mass spectrometry data from the mass spectrometer 10 (S601) and extracts valid data from the mass spectrometry data (S602). The inspection apparatus 200 may transmit valid data extracted through the network to the prediction apparatus 100 (S604). Alternatively, the inspection apparatus 200 may extract the peak data from the valid data (S603) and transmit the extracted peak data to the prediction apparatus 100 (S604). Generating valid data or peak data may follow the embodiment described based on FIG. 2.

The prediction apparatus 100 performs recognition on the data received from the inspection apparatus 200 (S605). Data recognition may include data pre-processing that converts the received data into an input array of deep neural networks. Generating an input array from valid data or peak data may follow the embodiment described based on FIG. 2.

The prediction apparatus 100 performs prediction on the recognized data (S606). The prediction may be performed based on a trained prediction model. Specifically, an output when the input array is input to the deep neural network may be generated as a prediction result.

The prediction apparatus 100 may generate inference data based on the prediction result (S607). A method of generating inference data will be described later with reference to FIG. 6.

The prediction apparatus 100 may transmit the inference data to the inspection apparatus 200 in operation S608 and the inspection apparatus 200 may output an inference result based on the received inference data in operation S609. For example, the inference result may be output through a monitor of the inspection apparatus 200.

In FIG. 6, it is described that valid data extraction and/or peak data extractions may be performed in the inspection apparatus 200 and input array generation is performed based on data received by the prediction apparatus 100.

According to embodiments, valid data extraction and/or peak data extraction may be set to be performed in the prediction apparatus 100 or input array generation may be set to be performed in the inspection apparatus 200. For example, the inspection apparatus 200 transmits mass spectrometry data to the prediction apparatus 100 and the prediction apparatus 100 generates valid data and extracts peak data based on the mass spectrometry data received from the inspection apparatus 200 and input array generation. Alternatively, inspection apparatus 200 may generate valid data, extract peak data, generate an input array, and set the inspection apparatus 200 to transmit the input array to the prediction apparatus 100.

The data predictor of the prediction apparatus 100 may be trained by a supervised learning method. According to the supervised learning method, only the data included in the output array can be output as a prediction result and data not assigned to the output node (or output array) cannot be output as the prediction result. As a result, there is a problem in that the correct answer cannot be output for data relating to a sample not assigned to the output node. In addition, even if the correct answer for the input sample is assigned to the output node, there is a possibility that an incorrect answer for the input sample is output due to an error of the deep neural network.

In order to improve the reliability of the prediction result, the prediction apparatus 100 may generate inference data with reference to the prediction results of the plurality of prediction models. To this end, the data predictor 130 may be configured to include a plurality of prediction models.

Example FIG. 7 is a flowchart illustrating a process of generating inference data, in accordance with embodiments. The input array generated through data recognition may be input to the deep neural network of the first prediction model and the deep neural network of the second prediction model, respectively, to obtain the first prediction result and the second prediction result (S701 and S702). That is, a plurality of prediction results may be obtained by inputting one input data into a plurality of prediction models. The first prediction model and the second prediction model may be set to walk sequentially. Alternatively, the first prediction model and the second prediction model may be set to allow parallel processing.

The first prediction result is compared with the second prediction result, and it is determined whether the second prediction result is a lower element or parity element to the first prediction result (S703).

For example, the first prediction result may be a prediction of a genus of bacteria, and the second prediction result may be a prediction of a species of bacteria. In this case, step S703 may be to determine whether the predicted bacterial species belong to the predicted bacteria. For this determination, a table defining the bacterial genus and bacterial species belonging to the genus may be predefined.

As another example, the first prediction result may indicate the type of cancer, and the second prediction result may predict the progress of a specific cancer. In this case, step S703 may be to determine whether the progress of the predicted specific cancer coincides with the predicted cancer. For example, if the second prediction result indicates that cancer has started for a specific cancer and the first prediction result indicates the specific cancer, it may be determined that the second prediction result is a sub-element of the first prediction result. Alternatively, when the first prediction result and the second prediction result indicate that both are normal, it may be determined that the first prediction result and the second prediction result are sibling elements.

If it is determined that the second prediction result is the lower or equivalence factor of the first prediction result, inference data including at least one of the first prediction result or the second prediction result may be generated (S704). On the other hand, if it is determined that the second prediction result is not a lower factor or parity factor of the first prediction result, inference data including the inference result indicating that the prediction has failed may be generated (S705). That is, when the first prediction result and the second prediction result are compared, when the first prediction result and the second prediction result are different, then it may be determined that the prediction result is not reliable, the inspection apparatus 200 predicts instead of the unreliable prediction result. As a result, a failure message may be output.

As described above, when the correct answer for the input sample is not assigned to the output node or due to an error of the deep neural network, an error may occur in the prediction result for the input sample. In order to improve prediction reliability, one can consider further training the prediction model. However, in consideration of difficulty in collecting clinical data, embodiments relate to a method of processing prediction tasks commissioned from a test apparatus into learning data. A method of generating training data for further training of the predictive model will be described with reference to the drawings.

Example FIG. 8 is a diagram illustrating a learning data management system, according to embodiments. The learning data management system may be in a form in which a verification device is added to the prediction system shown in FIG. 5. FIG. 9 is a flowchart illustrating a process of generating learning data in the verification apparatus. Based on FIG. 9, a method of generating learning data will be described in detail.

The verification apparatus generates verification data (S901). The verification data may include task identification information and correct answer information. The task identification information may be for identifying any one of a plurality of prediction tasks performed between the verification apparatus and the inspection apparatus. At least one of input data or inference data may be specified through the task identification information. The input data may include at least one of an input array input to a predictive model or mass spectrometry data, valid data, or peak data based on generating the input array.

The correct answer information may include at least one of information indicating whether the inference result is a correct answer, information indicating a correct answer to the input data, or information indicating an error between the inference result and the correct answer.

Answer information may be manually generated by a clinical expert. For example, when the clinical expert demonstrates clinical findings on the input data, the clinical findings of the clinical expert on the input data may be generated as correct answer information.

Alternatively, the correct answer information may be generated by comparing the inferred result with the clinical pathology data previously input. For example, the verification apparatus may receive clinical pathology data corresponding to task identification information from the clinical pathology system and generate correct answer information with reference to the clinical pathology data.

The verification apparatus may generate training data for predictive model learning based on the verification data in operation S902. For example, the training data may be generated based on the input array and the correct answer information generated based on the input array identified by the task identification information or the input data identified by the task identification information. The verification apparatus may receive an input array or input data identified by the task identification information from the inspection apparatus 200 or the prediction apparatus 100.

The training data based on the verification data, based on at least one of whether the inference result identified by the task identification information is the correct answer, or whether the error between the inference result identified by the task identification information and the correct answer is greater than or equal to a predefined value.

The verification apparatus 300 may transmit the data set including the learning data accumulated in the predetermined period or the predetermined number of learning data to the prediction apparatus 100. The prediction apparatus 100 may train the prediction model based on the data set received from the verification apparatus 300.

Further training on the predictive model may be performed according to predefined conditions. Here, the predefined condition may be a period or learning data associated with at least one value. For example, the verification apparatus 300 may transmit the accumulated learning data to the prediction apparatus 100 on a monthly or quarterly basis. Alternatively, the verification apparatus 300 may wait until a predetermined number of learning data samples accumulates and transmit the learning data to the prediction apparatus 100.

In FIG. 8, the verification apparatus 300 is illustrated as a different entity from the prediction apparatus 100. According to embodiments, the verification device 300 may be implemented as part of the prediction device 100. Alternatively, the verification apparatus 300 may be implemented as part of the inspection apparatus 200.

The prediction apparatus 100 may assign different versions to the prediction model before the additional training is performed and the prediction model after the additional training is performed. The prediction apparatus 100 may include a plurality of versions of the prediction model, and usage rights may be set for each version. For example, the first inspection apparatus 200 may receive the inference result using the first version of the prediction model, while the second inspection apparatus 300 may receive the inference result using the second version of the prediction model.

When the use authority of the inspection apparatus 200 is changed, the prediction apparatus 100 may check the inference result of the prediction task in which the inference result among the prediction tasks in the prediction model before the change is different from the inference result in the prediction model after the change. For example, when the use authority of the inspection apparatus 200 is changed from the first version of the prediction model to the second version of the prediction model, the inference result of the prediction tasks performed through the first version of the prediction model may be correction data for the prediction task having different inference results of the prediction model and may be transmitted to the inspection apparatus 200. The correction data may include task identification information and correction information. The correction information may include the result of inference in the prediction model of the second version.

In order to generate the correction data, the prediction apparatus 100 may store the input data and the inference result input to the prediction model of the first version.

Although the above-described embodiments are described based on a series of steps or flowcharts, this does not limit the time series order of the invention and may be performed simultaneously or in a different order as necessary. In addition, in the above-described embodiment, each component (for example, a unit, a module, etc.) constituting the block diagram may be implemented as a hardware device or software, and a plurality of components are combined into one hardware device or software. The above-described embodiments may be implemented in the form of program instructions that may be executed by various computer components, and may be recorded in a computer-readable recording medium. The computer-readable recording medium may include program instructions, data files, data structures, etc. alone or in combination. Examples of computer-readable recording media include magnetic media such as hard disks, floppy disks, and magnetic tape, optical recording media such as CD-ROMs, DVDs, and magneto-optical media such as floptical disks. media) and hardware devices specifically configured to store and execute program instructions, such as ROM, RAM, flash memory, and the like. The hardware device may be configured to operate as one or more software modules to perform the process according to the invention, and vice versa.

It will be obvious and apparent to those skilled in the art that various modifications and variations can be made in the embodiments disclosed. This, it is intended that the disclosed embodiments cover the obvious and apparent modifications and variations, provided that they are within the scope of the appended claims and their equivalents.

What is claimed is:

1. A method of producing a data set for prediction model training comprising:
   receiving mass spectrometry data of a sample;
   extracting valid data from the mass spectrometry data, wherein the valid data is within a predetermined range of mass-to-charge ratios;
   detecting at least one peak point from the valid data;
   obtaining peak data from the at least one peak point;
   generating an input array based on the peak data, wherein the input array is generated by converting the peak data for a deep neural network input;
   inputting the input array into the deep neural network and in response a prediction result is output;
   outputting a prediction result associated with the input array from the deep neural network; and
   generating inference data based on the prediction result.

2. The method of claim 1, wherein:
   the mass spectrometry data comprises a plurality of intensity values at a plurality of mass-to-charge ratios;
   the detecting the at least one peak point comprises comparing a first effective intensity value to neighboring effective intensity values, wherein the first effective intensity value and the neighboring effective intensity values that are determined from the plurality of intensity values; and
   determining that the first effective intensity value is one of the at least one peak point if the first effective intensity value is greater than the neighboring effective intensity values.

3. The method of claim 2, wherein the first effective intensity value and the neighboring intensity values are determined by subtracting a first reference value from the plurality of intensity values at the plurality of mass-to-charge ratios.

4. The method of claim 3, wherein:
   the plurality of intensity values comprises a first point and a second point having the first reference value at different mass-to-charge ratios;
   a first width of a range of mass-to-charge ratios is a difference of a mass-to-charge ratio of the first point and a mass-to-charge ratio of the second point; and
   when the first width between the first point and a second point is larger than a predetermined threshold value, then the reference value is updated to an intensity value of a third point and a fourth point, wherein a second width of a range of mass-to-charge ratios is a difference of a mass-to-charge ratio of the third point and a mass-to-charge ratio of a fourth point; and
   when the first width between the first point and the second point is smaller than the predetermined threshold value, the reference value is updated to an intensity value of a fifth point and a sixth point, wherein a third width of a range of mass-to-charge ratios is a difference of a mass-to-charge ratio of the fifth point and a mass-to-charge ration of the sixth point.

5. The method of claim 3, wherein:
   the peak data include a relative intensity value or a scaled relative intensity value of the at least one peak point;

the relative intensity value of the at least one peak point is determined based on the ratio between an intensity value of the at least one peak point and the reference value.

6. The method of claim 5, wherein an Nth data of the input array represents the relative intensity value or the scales relative intensity value of an Nth section of a preset range.

7. The method of claim 6, wherein there are a plurality of peak points in the Nth section comprising at least one of an average value, a maximum value, or a minimum value of the relative intensity value or the scaled relative intensity value of the plurality of peaks points which is set as the Nth data.

8. An apparatus comprising:
a data recognizer configured to convert peak data of a mass spectrometry result of an input sample into an input array for deep neural network input; and
a data predictor configured to input the input array into the deep neural network, output a prediction result for the input sample in response to the input, and generate inference data based on the prediction result.

9. The apparatus of claim 8, wherein the inference data is generated based on a first prediction result for the input array and a second prediction result for the input array.

10. The apparatus of claim 9, wherein:
when the first prediction result is a sub-element of the second prediction result, the data predictor is configured to generate the inference data to include at least one of the first prediction result or the second prediction result; and
when the first prediction result is not a sub-element of the second prediction result, the inference data is configured to include information indicating a prediction failure.

11. The apparatus of claim 10, wherein the first prediction result indicates a species of the input sample and the second prediction result indicates a genus of the input sample.

12. The apparatus of claim 8, wherein:
the data predictor trains the deep neural network based on learning data accumulated during a predetermined period or a predetermined number of learning data cycles;
the learning data comprises correct answer information for the input array and the input sample; and
the correct answer information is generated with reference to clinical data registered in a clinical pathology system.

13. The apparatus of claim 8, wherein:
the peak data comprises a relative intensity value or a scaled relative intensity value of a first peak point; and
the relative intensity value of the peak point is determined based on a ratio between a maximum value of effective intensity values of the first peak point and the effective intensity value of a second peak point.

14. The apparatus of claim 13, wherein an Nth data of the input array is characterized by representing a relative intensity value or a scales intensity value of an Nth interval of a predetermined range.

15. The apparatus of claim 14, wherein when a plurality of peak points exist in the Nth section, an average value, a maximum value, or a minimum vale of a relative intensity value or a scaled intensity value of the plurality of peaks points is set as the Nth data.

\* \* \* \* \*